United States Patent [19]

Watanabe et al.

[11] 4,414,336
[45] Nov. 8, 1983

[54] METHOD FOR PREPARING SAMPLE FOR USE IN ENDOTOXIN TEST

[75] Inventors: Ryozo Watanabe, Takatsuki; Keiichi Kawasumi, Hirakata; Shoichi Maeda, Osaka; Takashi Shoji, Tondabayashi, all of Japan

[73] Assignee: The Green Cross Corporation, Osaka, Japan

[21] Appl. No.: 306,647

[22] Filed: Sep. 29, 1981

[30] Foreign Application Priority Data

Jan. 28, 1981 [JP] Japan ................... 56-11204
Jan. 28, 1981 [JP] Japan ................... 56-11205

[51] Int. Cl.$^3$ ................ G01N 33/48; G01N 33/54
[52] U.S. Cl. ................... 436/502; 210/635; 210/927; 436/178; 436/825
[58] Field of Search ............ 436/502, 825, 178; 210/635, 927

[56] References Cited

U.S. PATENT DOCUMENTS

| | | | |
|---|---|---|---|
| 3,944,391 | 3/1976 | Harris et al. | 436/502 |
| 4,107,077 | 8/1978 | Sullivan et al. | 436/502 |
| 4,138,474 | 2/1979 | Updike | 210/635 X |
| 4,273,557 | 6/1981 | Juranas | 436/502 |
| 4,276,050 | 6/1981 | Firca et al. | 436/502 |
| 4,279,774 | 7/1981 | Lindsay et al. | 436/502 |
| 4,350,760 | 9/1982 | Nicolas et al. | 210/635 |

FOREIGN PATENT DOCUMENTS 56-40758 4/1981 Japan ................... 210/635

OTHER PUBLICATIONS

Schenkein et al., "The Journal of Clinical Investigation", vol. 50, 1971, pp. 1864–1868.

*Primary Examiner*—Arnold Turk
*Attorney, Agent, or Firm*—Cushman, Darby & Cushman

[57] ABSTRACT

(1) A method for preparing a sample for use in the endotoxin test which comprises subjecting a sample of plasma or blood preparation to a contact with water-insoluble anti-human $\alpha_2$-macroglobulin antibody and to a gel filtration by means of a gel of allyl dextran cross-linked with N,N'-methylenebis acrylamide or a gel of polyvinyl alcohol having many hydrophilic hydroxyl groups, and recovering the maximum molecular weight fraction.

(2) A kit for preparing a sample for use in the endotoxin test consisting of a set of a sample-developing column prepared by packing a water-insoluble anti-human $\alpha_2$-macroglobulin antibody and a gel of allyl dextran cross-linked with N,N'-methylenebis acrylamide or a gel of polyvinyl alcohol having many hydrophilic hydroxyl groups, both equilibrated with a buffer solution of pH 7.0–7.4, into a column and tightly sealing the column, an aqueous solution of a high molecular colored substance to be added to the sample and a buffer solution for use in developing the sample.

7 Claims, 1 Drawing Figure

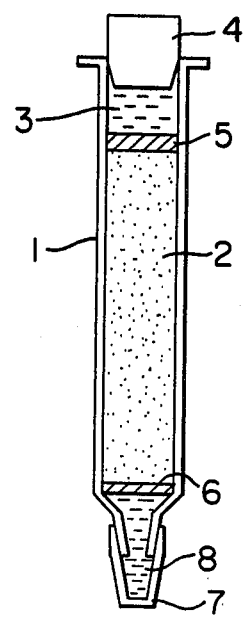

METHOD FOR PREPARING SAMPLE FOR USE IN ENDOTOXIN TEST

This invention relates to a method for preparing a sample for use in the endotoxin test and to a kit for preparing said sample. More particularly, this invention relates to a method for preparing a sample for use in the Limulus amebocyte lysate test (hereinafter referred to as "Limulus test") for the purpose of testing the endotoxin in plasma or blood preparations, and a kit for preparing said sample.

Since the method using Limulus amebocyte lysate was reported by Levin in 1968 for the in vitro detection of bacterial endotoxin, the detection of endotoxin in blood, cerebrospinal fluid and urine has been studied by many researchers from the viewpoint of application to clinical diagnoses.

Regarding the Limulus test of cerebrospinal fluid and urine, it is reported that there is substantially no problem and the measurement can be carried out sufficiently in accordance with the endotoxin sensitivity of the Limulus lysate used. However, many problems remain unsolved when endotoxin in blood is measured with Limulus lysate. That is, blood contains an inhibitory substance and a pseudo-positive substance to Limulus reaction, and the many studies conducted with the aim of removing them cannot yet be said to have accomplished this object completely. Therefore, according to the hitherto published reports concerning the test using such unsatisfactory method, it is the actual state that the result of the Limulus test does not always coincide with the clinical symptoms or the result of bacterial cultivation of blood so that the usefulness of the Limulus test applied to blood sample is distrusted.

In view of the above, the present inventors conducted various studies on the method for pretreating the plasma sample and blood preparation sample to be subjected to the Limulus test. That is, the inventors studied a method for effectively removing the substances inhibitory or pseudo-positive to Limulus reaction from said samples and for thereby preparing a sample for endotoxin measurement with which the nonspecific reaction at the time of the Limulus test can be eliminated and the sensitivity of measurement can be enhanced. As the result, it was found that a sample having excellent sensitivity can be prepared by a simple pretreatment which comprises subjecting plasma or blood preparation to a contact with a water-insoluble anti-human $\alpha_2$-macroglobulin antibody and to a gel filtration by means of a gel of allyl dextrin crosslinked with N,N'-methylenebis acrylamide or a gel of polyvinyl alcohol having many hydrophilic hydroxyl groups. At the same time, the inventors succeeded in making a kit for preparing said sample from a column for developing the sample, an aqueous solution of a high molecular colored substance added to the sample and a buffer solution for developing the sample. Based on these facts, this invention was accomplished.

It is an object of this invention to provide a method for preparing a sample for use in the endotoxin test.

It is another object of this invention to provide a kit for preparing a sample for use in the endotoxin test.

Other objects and advantages of this invention will become apparent from the description given below.

The drawing attached is a plan sectional view of an example of the column for filtering the sample of this invention, wherein the numerical figures represent the following: 1—column, 2—packing material, 3—supernatant, 4—stopper for tight sealing, 5—gel-repressing filter plate, 6—gel-supporting filter plate, 7—bottom cap, 8—buffer solution layer.

According to this invention, there is provided a method for preparing a sample for use in the endotoxin test which comprises subjecting a sample of plasma or blood preparation to a contact with a water-insoluble anti-human $\alpha_2$-macroglobulin antibody and to a gel filtration by means of a gel of allyl dextran crosslinked with N,N'-methylenebis acrylamide or a gel of polyvinyl alcohol having many hydrophilic hydroxyl groups and recovering the maximum molecular weight fraction.

Further, according to this invention, there is also provided a kit for preparing a sample for use in the endotoxin test which consists of a set of a sample developing column prepared by packing a water-insoluble anti-human $\alpha_2$-macroglobulin antibody and a gel of allyl dextran crosslinked with N,N'-methylenebis acrylamide or a gel of polyvinyl alcohol having many hydrophilic hydroxyl groups, both equilibrated with a buffer solution of pH 7.0–7.4, into a column and tightly sealing the column, an aqueous solution of a high molecular weight colored substance to be added to the sample and a buffer solution for use in developing the sample.

The carrier for use in gel filtration in this invention is a gel of allyl dextran crosslinked with N,N'-methylenebis acrylamide or a gel of polyvinyl alcohol having many hydrophilic hydroxyl groups. It should be a material capable of passing, as a maximum molecular weight fraction, the substances having a molecular weight of 300,000 or higher present in plasma or blood preparations. As examples of said carrier, those having a network structure of 100–300 mesh and preferably 150–250 mesh, as well as those having the effect of molecular sieve, can be referred to. A preferable example of gel belonging to the former type is Sephacryl S 300 (manufactured by Pharmacia Fine Chemicals Co.) and preferable examples belonging to the latter type are TOYOPEARL HW-60 and HW-65 (manufactured by Toyo Soda K.K.).

The term "water-soluble anti-human $\alpha_2$-macroglobulin antibody" means a product prepared by making an anti-human $\alpha_2$-macroglobulin antibody insoluble in water. As one example of such antibodies, a product prepared by chemically combining anti-human $\alpha_2$-macroglobulin antibody with a water-insoluble carrier and thereby making the antibody insoluble in water can be referred to. As examples of the carrier used for making the antibody water-insoluble, there can be referred to activated polyacrylamide gel [for example, Bio-gel P-300: sold by Bio-gel Co., USA], agarose [for example, Sepharose 4B: sold by Pharmacia Fine Chemicals Co., Sweden], crosslinked dextrans [for example, Sephadex G 200: sold by Pharmacia Fine Chemicals Co.], allyl dextran crosslinked with N,N'-methylenebis acrylamide [for example, Sephacryl S 300: sold by Pharmacia Fine Chemicals Co.] and polyvinyl alcohol gel [for example, TOYOPEARL HW-60: sold by Toyo Soda K.K.]. Said activation is usually effected by a treatment with cyanogen bromide. Among them, there are recommended as more preferable water-insoluble carriers, allyl dextran crosslinked with N,N'-methylenebis acrylamide and polyvinyl alcohol gel.

The method of treating a carrier with cyanogen bromide has already been established as a method for separating proteins by the technique of affinity chromatography proposed by P. Cuatrecasas and C. B. Anfinsen [Methods in Enzymology, XXII, ed. by Jakoby. W. B., pp 345 (1971)].

The reaction between the carrier having the combining ability thus obtained and the anti-human $\alpha_2$-macroglobulin antibody can be carried out at pH 6 to 8 at about 3° to 25° C.

Anti-human $\alpha_2$-macroglobulin antibody can be obtained by administering $\alpha_2$-macroglobulin as an immunogen to an appropriate animal such as guinea pig, rat, hamster, sheep, horse, house rabbit and the like, and after the immunization, recovering the antiserum, separating anti-human $\alpha_2$-macroglobulin antibody from said antiserum and purifying it.

The $\alpha_2$-macroglobulin as an immunogen can be obtained, for example, by the method mentioned in "The Plasma Proteins", edited by Frank Putnam, pp. 246–257, Academic Press, through it is not limited to this method by any means.

In administering the immunogen, Freund's complete adjuvant may be used in combination, and an additional immunization may also be carried out (for example, it may be repeated several times at intervals of several weeks). The produced anti-human $\alpha_2$-macroglobulin antibody is recovered by a method well known in itself, such as the method of E. J. Cohn [J. Am. Chem. Soc., 68, 459 (1946)], the method of J. H. Northrop et al. [J. Gen. Physiol., 32, 705 (1949)], the method of A. M. Pappenheimer et al. [J. Exp. Med., 71, 247 (1940)], etc. It is also allowable at this time to extract the $\gamma$-globulin fraction by, for example, the Cohn's low temperature alcohol fractionating method [E. J. Cohn, et al., J. Am. Chem. Soc., 62, 3386 (1940)].

The anti-human $\alpha_2$-macroglobulin antibody thus obtained is made insoluble in water with the fixing carrier, whereby a fixed anti-human $\alpha_2$-macroglobulin antibody or a water-insoluble anti-human $\alpha_2$-macroglobulin antibody can be obtained.

The water-insoluble anti-human $\alpha_2$-macroglobulin antibody thus obtained is mixed with the above-mentioned carrier for gel filtration and then uniformly packed into a column. The proportion of the water-insoluble anti-human $\alpha_2$-macroglobulin antibody in the packing material is adjusted to 5–20% W/W and more preferably to 7–15% W/W. At this time, it is preferable that the carrier for gel filtration is the same as the carrier used for making the anti-human $\alpha_2$-macroglobulin antibody insoluble in water.

By subjecting a sample of plasma or blood preparation to gel filtration by the use of such a packing material, namely by subjecting the sample to a contact with water-insoluble anti-human $\alpha_2$-macroglobulin antibody and to a gel filtration with an appropriate carrier, endotoxin is concentrated into the maximum molecular weight fraction but the inhibitory substances and the pseudo-positive substance do not come into said fraction. Therefore, an excellent sample for use in Limulus test can be obtained.

The gel filtration can be carried out by a means well known in itself.

The diameter of the sample-developing column used in this invention may be any diameter, so far as it is a diameter employed in blood tests. In order to enhance the accuracy of the test, however, a diameter of 7–12 mm is preferable. The packing material to be packed therein is the above-mentioned carrier for gel filtration and the water-insoluble anti-human $\alpha_2$-macroglobulin antibody. The packing material is previously made negative to endotoxin and then put to use. Before introducing the packing material into the column, it is equilibrated with a buffer solution of pH 7.0–7.4 and preferably pH 7.0 such as phosphate buffer solution. The volume packing material to be packed into the column is 2–4 ml and preferably 2.2–3 ml when the diameter of the column to be used is 7–12 mm. After packing it into the column, a small amount (about 2 ml) of the buffer solution is left as a supernatant over the gel, and the column is tightly sealed for the purpose of preventing it from drying. Preferably, a buffer solution layer filled with said buffer solution is provided under the gel. All the buffer solutions used in this invention preferably contain a bactericide. For example, it is preferable to suppress the multiplication of bacteria by adding 0.1% of bromonitroalcohol thereto. The column thus prepared is kept vertical without turning it upside down till the time when it is put to use.

As the buffer solution for developing the sample, a buffer solution of pH 7.0–7.4 and preferably pH 7.0, such as phosphate buffer solution, is usually employed. Usually the buffer solution for this purpose is the same as the buffer solution for equilibrating the packing material. The buffer solution for developing the sample also has to be negative to endotoxin. As a treatment for making it negative to endotoxin, the treatment which comprises previously heating the crystalline phosphate from which the buffer solution is to be prepared, at 180° C. for 10 hours or more, can be referred to, for example. The heat-treated buffer solution is divided into 10–20 ml portions for every kit, tightly sealed and then sterilized.

The high molecular weight colored substance added to the sample serves as an endotoxin marker at the time of developing the sample by means of the column. Any substance may be used in this invention, so far as it has the function of such a marker. Concretely, said high molecular weight colored substance is a substance having an average molecular weight of 300,000 or higher, of which preferable examples include blue dextran (Cibacron Blue F3GA-Dextran, dextran substituted with Cibacron Blue F3GA) and the like. This substance also has to be negative to endotoxin. This substance is adjusted to a concentration of 1–4% W/V and preferably 2% W/V by the use of a buffer solution of pH 7.0–7.4 and more preferably pH 7.0 such as phosphate buffer solution, after which it is divided into 1–5 ml portions for every kit and tightly sealed. The aqueous solution containing the high molecular weight colored substance is used by adding it in an amount of about 0.1 ml to 1 ml of the sample.

As examples of blood preparation, albumin, immune globulin, fibrinogen, blood coagulation factor and the like can be referred to. They are not limited to those obtained from blood, but those obtained from placenta or the like may also be used.

The kit according to this invention is used in the following manner. Thus, first of all, the sealed column packed with the water-insoluble anti-human $\alpha_2$-macroglobulin antibody and the carrier for gel filtration is unsealed and stood vertically to make it ready for development. The supernatant buffer solution remaining over the packing material is removed by the use of a pipette or by developing it, after which 0.1 ml of a test solution previously prepared by adding about 0.1 ml of an aqueous solution of high molecular weight colored substance to 1 ml of sample (for example, plasma) is charged into the upper part of the column. Then development is carried out. When the supernatant has disappeared, 0.5–1.5 ml of the buffer solution for developing the sample is poured into the column to develop the sample.

Thereby, endotoxin and the high molecular weight colored substance are developed on the column as the maximum molecular weight fraction of the developed sample and form a quite clear and very thin band. After rejecting about 0.7–1.0 ml (usually 0.7 ml) of the firstly developed fraction, about 0.3–0.7 ml (usually 0.5 ml) of the subsequently flowing out maximum molecular weight fraction containing the high molecular colored substance as a marker is recovered as a sample for the Limulus test. This treatment necessitates a time period of about 20 minutes.

Inhibitory substances and pseudo-positive substances have already been removed from the sample for the endotoxin test thus prepared, so that the sample can be put to the hitherto known Limulus test with usefulness.

Outline of the Limulus test is as follows. Thus, a freeze-dried preparation of Limulus Ameboctye lysate is dissolved in 5 ml of water, divided into 0.1 ml portions and poured into sealable test tubes in ice water. To each test tube is added 0.1 ml of the sample for the endotoxin test, which has been subjected to the treatment of this invention, in ice water. After homogenization, the content of the test tube is incubated for about 1 hour in a warm bath having a temperature of 37° C., while avoiding shaking. If endotoxin is present in the sample, the test solution is gelatinized by this treatment, so that the test solution remains at the tube bottom when the test tube is overturned to an angle of 180°. In such a case, the sample tested is evaluated as positive. If the test solution flows down along the wall upon 180° overturn, the sample is evaluated as negative. When a sample prepared according to the method of this invention or by the use of the kit of this invention is tested, the endpoint of measurement is 0.3 ng/ml as expressed by endotoxin content in plasma, which means that the method of this invention is quite superior in sensitivity to the hitherto known experimental method of which sensitivity is 0.9±0.45 ng/ml.

The kit of this invention thus provided is a novel kit which has not existed in the past, and makes a very great contribution to the practical application of the Limulus test.

Hereunder, this invention will be explained in more detail with reference to the samples of this invention and comparative experimental examples, but the invention is not limited by these examples.

EXAMPLE 1

[Column for Developing Sample]

Packing material 2 [2 ml of 10:1 mixture of Sephacryl S-300 (manufactured by Pharmacia Fine Chemicals Co.) and anti-human $\alpha_2$-macroglobulin antibody-Sephacryl S-300] equilibrated with 0.1 M phosphate buffer solution containing 0.1% of Bronopol (a trade name of bromonitropropandiol sold by Green Cross Corp.) and having a pH value of 7.0 where packed into column 1 having a diameter of 9 mm (gel capacity 2.5 ml) such as shown in the attached drawing, and the column was tightly sealed with stopper 4. These procedures were carried out aseptically.

In the drawing, supernatant 3 is the residual portion of the above-mentioned buffer solution. 5 is a gel-repressing filter plate and 6 is a gel-supporting filter plate, and the distance from 5 to 6 is 40 mm. 7 is a bottom cap for unsealing the column. 8 is a layer of buffer solution.

[Aqueous Solution of High Molecular Weight Colored Substance Added to Sample]

Blue dextran (Cibacron Blue F3GA-Dextran, sold by Seikagaku Kogyo K.K.) was heat-treated in a nitrogen atmosphere at 180° C. for 10 hours, dissolved into 0.1 M phosphate buffer solution having a pH value of 7.0 to a concentration of 2% W/V, divided into 2 ml portions for every kit, and then heat-sterilized at 121° C. for 20 minutes. [Buffer Solution for Developing Sample]

A 0.1 M phosphate buffer solution of pH 7.0 prepared by the use of an endotoxin-free phosphate was heat-treated at 121° C. for 20 minutes and divided into 10 ml portions for every kit.

Example 2

[Column for Developing Sample]

Packing material 2 [2 ml of 13:1 mixture of TOYO-PEARL HW-60 (manufactured by Toyo Soda K.K.) and anti-human $\alpha_2$-macroglobulin antibody-TOYOPEARL HW-60] equilibrated with 0.1 M phosphate buffer solution containing 0.1% of Bronopol and having a pH value of 7.0 were packed into column 1 having a diameter of 9 mm (gel capacity 2.5 ml) shown in the attached drawing, and the column was tightly sealed with stopper 4. These procedures were carried out aseptically.

In the drawing, supernatant 3 is the residual portion of the above-mentioned buffer solution, 5 is a gel-repressing filter plate, 6 is a gel-supporting filter plate and the distance from 5 to 6 is 40 mm. 7 is a bottom cap for unsealing the column, and 8 is a layer of buffer solution.

[Aqueous Solution of High Molecular Weight Colored Substance Added to Sample]

Blue dextran (Cibacron Blue F3GA-Dextran, sold by Seikagaku Kokyo K.K.) was heat-treated in an atmosphere of nitrogen at 180° C. for 10 hours, dissolved into a 0.1 M phosphate buffer solution having a pH value of 7.0 to a concentration of 2% W/V, and divided into 2 ml portions for every kit. Then it was sterilized with heat at 121° C. for 20 minutes.

[Buffer Solution for Developing Sample]

A 0.1 M phosphate buffer solution of pH 7.0 prepared by the use of an endotoxin-free phosphate was heat-treated at 121° C. for 20 minutes and then divided into 10 ml portions for every kit.

Experimental Example

As sample, a human plasma (A) treated with the kit mentioned in the foregoing examples (the column shown in the drawing) was used. As control samples, a chloroform-treated human plasma (B) (a sample prepared by mixing equal quantities of chloroform and human plasma, shaking and stirring the mixture at room temperature for 2 hours, centrifuging the mixture for 10 minutes at a rotation speed of 2,000 r.p.m. and taking out the middle layer), a plasma (C) which has been treated only with Bio-Gel P-200 (a trade name of polyacrylamide gel, manufactured by Bio-Rad Co.) in the same manner as above in place of using the mixed packing material of the kit of this invention, and a human plasma diluted and heat-treated (D) (prepared by diluting human plasma to three times its volume and then heat-treating it in a bath of 100° C. for 10 minutes) were used. The samples were subjected to the Limulus test, and the endpoints (ng/ml plasma) were determined. In the test, Pyrosate (trade name of endotoxin-detecting reagent manufactured by Green Cross Corporation) was used. The procedure of detection was as follows. Thus, the solution to be tested, the negative control solution (distilled water for injection according to the Japanese Pharmacopeia) and the positive control solution, 0.1 ml each, were added to each of the reaction test tubes containing 0.1 ml of endotoxin-detecting reagent. The tubes were stopped and the contents were gently stirred and mixed so as to form no foam, while cooling the tubes in ice. After the mixing, the tubes were incubated at 37° C. for 1 hour. Thereafter, they were overturned slowly to an angle of 180° to evaluate the occurrence of coagulation, from which endpoints of the samples were determined. The results were as shown in Table 1.

TABLE 1

| Method of treatment | Endpoint (ng/ml) |
|---|---|
| A (This invention) | 0.3 ± 0.4 |
| B | 1.4 ± 0.8 |
| C | 0.9 ± 0.4 |
| D | 1.9 ± 0.7 |

As the result, a great increase in sensitivity was achieved by the use of the kit of this invention. Further, the treatment was completed in about 20 minutes when the kit of this invention was used, whereas the treatment took 1-2 hours according to the treating method of (C).

What is claimed is:

1. A method for preparing a sample for use in endotoxin test which comprises subjecting a sample of plasma or blood preparation to a contact with water-insoluble anti-human $\alpha_2$-macroglobulin antibody and to a gel filtration by means of a carrier for gel filtration which is a gel of allyl dextran crosslinked with N,N'-methylenebis acrylamide or a gel of polyvinyl alcohol having many hydrophilic hydroxyl groups and recovering the maximum molecular weight fraction.

2. A method according to claim 1, wherein said water-insoluble anti-human $\alpha_2$-macroglobulin antibody is a product obtained by chemically combining anti-human $\alpha_2$-macroglobulin antibody with a water-insoluble carrier.

3. A method according to claim 1, wherein said water-insoluble carrier is activated polyacrylamide gel, agarose, crosslinked dextran, allyl dextran crosslinked with N,N'-methylenebis acrylamide or polyvinyl alcohol gel.

4. A method according to claim 3, wherein said water-insoluble carrier is activated allyl dextran crosslinked with N,N'-methylenebis acrylamide or activated polyvinyl alcohol gel.

5. A method according to claim 3 or 4, wherein said activation is carried out by a treatment with cyanogen bromide.

6. A method according to claim 1, wherein the grain size of the carrier for gel filtration is 100–300 mesh.

7. A method according to claim 1, wherein said anti-human $\alpha_2$-macroglobulin antibody is a product obtained by administering $\alpha_2$-macroglobulin as an immunogen to guinea pig, rat, hamster, sheep, horse or house rabbit, and after the immunization, recovering the antiserum, separating the anti-human $\alpha_2$-macroglobulin antibody from said antiserum and purifying the antibody.

* * * * *